(12) United States Patent
Rozga et al.

(10) Patent No.: US 6,242,248 B1
(45) Date of Patent: Jun. 5, 2001

(54) BIOREACTOR AND RELATED METHOD

(75) Inventors: Jacek Rozga, Westlake Village; Achilles A. Demetriou, Bel Air, both of CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 09/500,158

(22) Filed: Feb. 8, 2000

(51) Int. Cl.$^7$ ........................................ C12M 1/12
(52) U.S. Cl. .................. 435/297.4; 435/182; 435/383; 435/400; 435/401; 435/260
(58) Field of Search ................... 435/297.4, 1.3, 435/182, 383, 400, 401, 420, 260, 284.1, 357.1

(56) References Cited

U.S. PATENT DOCUMENTS

| | | |
|---|---|---|
| 3,997,396 | 12/1976 | Delente . |
| 4,184,922 | 1/1980 | Knazek et al. . |
| 4,647,539 | 3/1987 | Bach . |
| 4,804,628 | 2/1989 | Cracauer et al. . |
| 4,889,812 | 12/1989 | Guinn et al. . |
| 5,110,741 | 5/1992 | Ohi et al. . |
| 5,622,857 | * 4/1997 | Goffe ................................. 435/378 |
| 5,712,154 | 1/1998 | Mullon et al. . |

FOREIGN PATENT DOCUMENTS

| | | |
|---|---|---|
| 0 343 394 | 11/1989 | (EP) . |
| WO 86/02379 | 4/1986 | (WO) . |

\* cited by examiner

Primary Examiner—David A. Redding
(74) Attorney, Agent, or Firm—Sidley & Austin

(57) ABSTRACT

A bioreactor (10) has arranged within its internal chamber (14) a bundle of liquid-impermeable hollow tubes (16), which are used to freeze or vitrify a biologically active material seeded within the internal chamber. When the bioreactor is ready for use, the biologically active material may be thawed by perfusing the liquid-impermeable hollow tubes with a heated solution or heated vapor.

24 Claims, 2 Drawing Sheets

BIOREACTOR AND RELATED METHOD

BACKGROUND OF THE INVENTION

1. Field of the Invention

The present invention relates generally to the field of cell and molecular biology and microbiology, and, more particularly to a bioreactor and related method. Although the invention is subject to a wide range of applications, it is especially suited for use in perfusion cell culture and bio-artificial organs, and will be particularly described in that environment.

2. Description of the Related Art

Traditionally, cell have been grown on a nutrient medium spread over a two-dimensional plastic culture dish. Bioreactors provide an alternative means for culturing cells, which is more efficient and manageable.

Bioreactors come in many shapes and sizes, and serve various functions in addition to conventional cell culturing, including, artificial organs and bioremediation units. In conventional bioreactors, hollow fibers traverse the length of an enclosed cylindrical shell. A cell and culture medium mixture is injected into the shell. The cells typically settle on the outer surface of the hollow fibers. Nutrients and oxygen flow through the intracapillary space of the hollow fibers, and they diffuse across the walls of the hollow fibers to nourish the cells.

Current commercially available bioreactors typically require the user to seed the unit with the desired cells or tissue, as it is difficult for manufacturers of bioreactors to deliver a pre-fabricated bioreactor that contains viable cells or tissue. To offer a bioreactor with viable cells or tissue already in place, a manufacturer must somehow preserve the cells or tissue located within the shell, such that the cells remain temporarily inactive without destroying cell viability, and provide a mechanism for reactivating the cells. Such a result may be accomplished by rapidly and uniformly freezing the bioreactor, and thawing the bioreactor when it is ready to use. The freezing preferably should occur at a uniform and high cooling rate, also referred to as vitrification, because a non-uniform or low-rate freezing can lead to the creation of ice crystals, a byproduct which destroys a large number of cells, and incidently leads to fluid volume expansion which may burst the bioreactor.

The rapid uniform freezing or vitrification process, which maximizes cell viability, is not easily accomplished with conventional hollow-fiber bioreactors. For example, a typical bioreactor is approximately 3 to 4 inches in diameter and can be submerged into liquid nitrogen to freeze the bioreactor. This method, however, freezes the outer layer of liquid contained within the shell, which thus acts as an insulator, leaving the core, where the cells have settled, unfrozen.

Thus, a need exists for a desirable pre-fabricated, vitrified bioreactor seeded with viable cells or tissue that is in a ready-to-use state. Such a bioreactor can alleviate the nuisance and expense of the user having to assemble and seed the bioreactor, with its attendant sterility and fabrication requirements, whether used for cell culture, biomedical, or other purposes.

BRIEF SUMMARY OF THE INVENTION

The present invention, which addresses this need, provides a prefabricated and seeded bioreactor which is ready-to-use once thawed.

According to the present invention, biologically active material in the internal chamber of a bioreactor is frozen or vitrified. This is accomplished by arranging a bundle of liquid-impermeable hollow tubes in the internal chamber and perfusing an ultra-coolant substance through the intratubular space of the hollow tubes. When the bioreactor is ready to use, the biologically active material may be thawed by perfusing the liquid-impermeable hollow tubes with a heated solution or heated vapor. The hollow tubes may also be gas-impermeable Other features and advantages of the present invention will be set forth in part in the description which follows and accompanying drawings, wherein the preferred embodiments of the invention are described and shown, and in part become apparent to those skilled in the art upon examination of the following detailed description taken in conjunction with the accompanying drawings, or may be learned by practice of the invention. The advantages of the invention may be realized and attained by means of the instrumentalities and combinations particularly pointed out in the appended claims.

DESCRIPTION OF THE PREFERRED EMBODIMENTS

Figure 1:
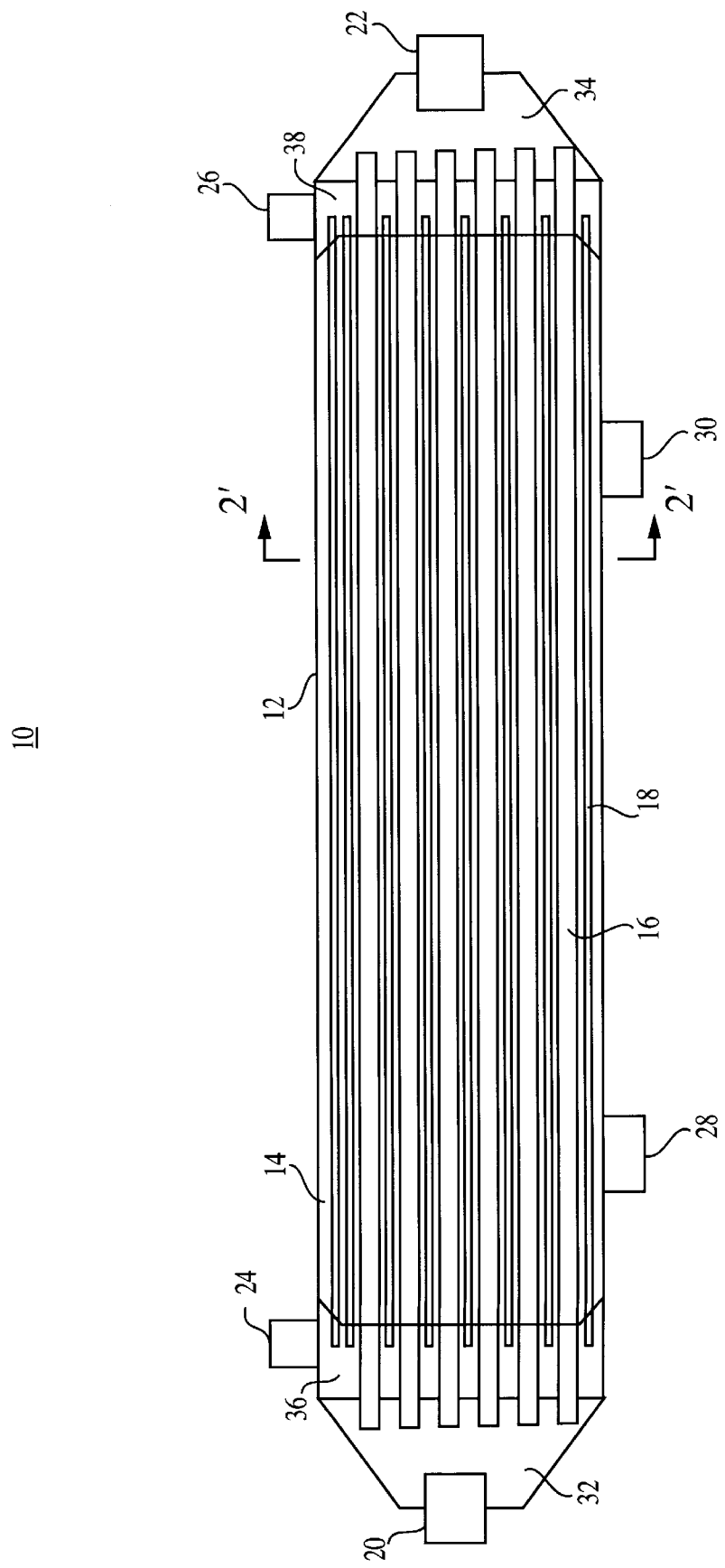
FIG. 1 is a cross-sectional view of a schematic depiction of a bioreactor configured according to the present invention.

As shown in the exemplary drawings, and with particular reference to FIG. 1, which is a cross-sectional view of a schematic depiction of a bioreactor configured according to the present invention, the bioreactor 10 comprises a shell 12 defining an internal chamber 14, a bundle of hollow tubes 16, and a bundle of hollow fibers 18. Further, the bioreactor includes a hollow tube inlet port 20, a hollow tube outlet port 22, a hollow fiber inlet port 24, a hollow fiber outlet port 26, a cell inlet port 28, and a cell outlet port 30.

In the preferred embodiment, the shell 12 can be made of a material that is capable of withstanding freezing or vitrification, such as, rigid plastic, and can be cylindrical in shape. Other materials and shapes may be utilized depending on the application. The volume and shape can vary according to the number of cells or tissue to be seeded into the unit. The diameter of the shell of the present invention may be larger in diameter than typical dual-fiber bioreactors that achieve the same or similar biological function, in order to accommodate the hollow tubes which, as described below, are correspondingly larger in diameter than typical hollow fibers commonly utilized in the art.

The internal chamber 14 can be divided to form a hollow tube perfusion inlet compartment 32, a hollow tube perfusion outlet compartment 34, a hollow fiber perfusion inlet compartment 36, and a hollow fiber perfusion outlet compartment 38. These compartments serve as manifolds to distribute and collect the fluid and the perfusate entering and exiting the ends of the hollow tubes 16 and hollow fibers 18, respectively.

The cell inlet port 28 and the cell outlet port 30 are in communication with the internal chamber 14. The cell inlet port is configured to admit a mixture of a biologically active material suspended in a culture medium into the internal chamber. Preferably, the mixture will include a cryoprotectant solution to assist in preventing crystallization of the biologically active material during freezing or vitrification. The cell outlet port is configured to exit the mixture from the internal chamber. A skilled artisan will appreciate the composition of the biologically active material, culture medium, and cryoprotectant solution can vary with the application for the bioreactor. For example, the biologically active material can be, for example, cells, tissue, fragments thereof, or microorganisms, such as, bacteria or fungi. The culture medium can be selected according to the biologically active material to be seeded in the reactor. The cryoprotectant solution can be, for example, a 10% solution of methylsulfoxide.

Figure 2:
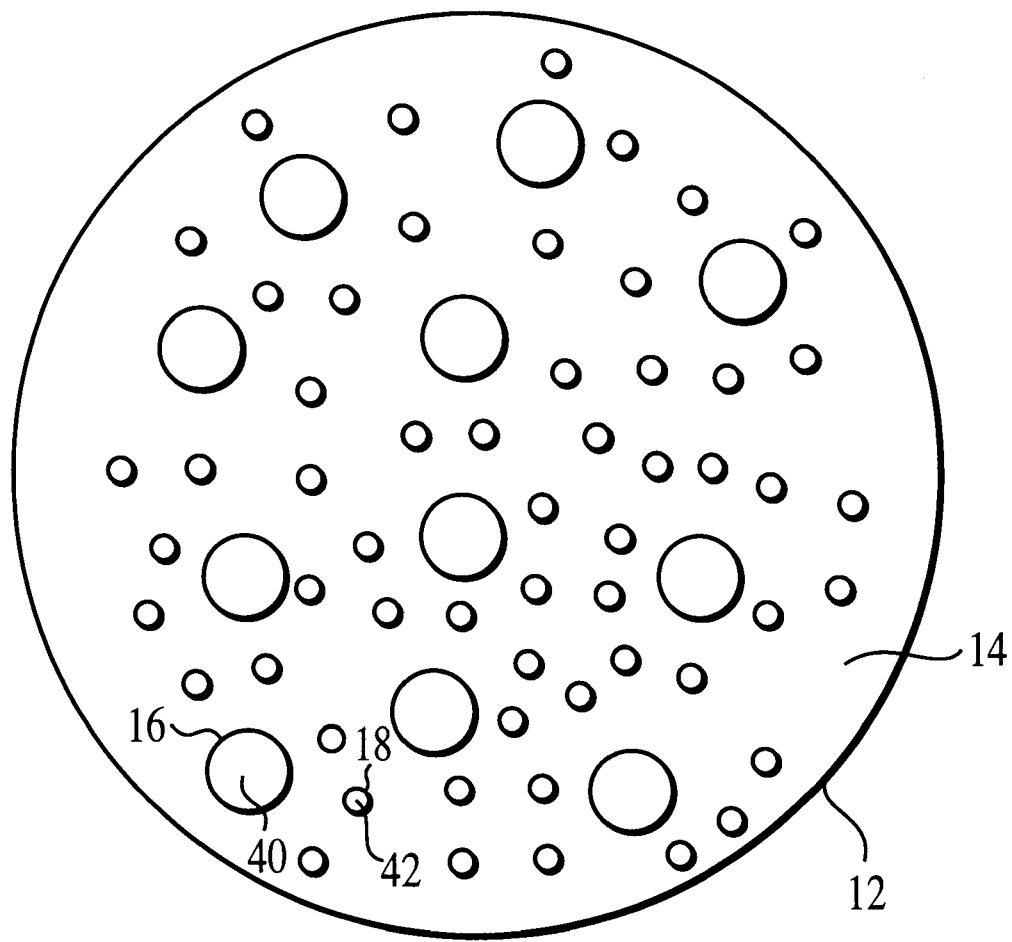
FIG. 2 is a cross sectional view of the complete bioreactor shown in FIG. 1, taken along the plane indicated by broken line 2'—2'.

Referring to FIG. 2, the hollow fibers 18 are disposed within the internal chamber and their walls define an intracapillary space 42. The respective ends of the fibers extend from inside the hollow fiber perfusion inlet compartment 36 to inside the hollow fiber perfusion outlet compartment 38. The fibers can be composed of a commonly used liquid-permeable material capable of withstanding freezing or vitrification, for example, polysulfone. A skilled artisan will appreciate that the material, size, arrangement, and number of tubes can vary with the application for the bioreactor, but preferably have an inside diameter of at least 500 microns and a wall thickness of at least 50 microns.

The hollow fiber perfusion inlet compartment 36 is in communication with the intracapillary space 42 and the hollow fiber inlet port 24, and is configured to isolate an entering perfusate from the internal chamber 14 and the intratubular space 40. The hollow fiber perfusion outlet compartment 38 is in communication with the intracapillary space and the hollow fiber outlet port 26, and is configured to isolate the exiting perfusate from the internal chamber and the intratubular space.

The hollow fiber inlet port 24 is in communication with the intracapillary space 42, via the hollow fiber perfusion inlet compartment 36, and configured to admit the perfusate into the intracapillary space. The hollow fiber outlet port 26 is in communication with the intracapillary space, via the hollow fiber perfusion outlet compartment 38, and is configured to exit the perfusate from the intracapillary space. A skilled artisan will appreciate the perfusate can vary with the application for the bioreactor. For example, the perfusate can be a culture medium, blood, or plasma.

The hollow tubes 16 are disposed within the internal chamber 14 and their walls define an intratubular space 40. (See FIG. 2.) In the illustrated embodiment, the respective ends of the tubes extend from inside the hollow tube perfusion inlet compartment 32 to inside the hollow tube perfusion outlet compartment 34. The tubes can preferably be composed of a commonly used liquid-impermeable material that is capable of withstanding freezing or vitrification, for example, Teflon. Optionally, the hollow tubes can also be gas-impermeable and made of a material such as silicone. A skilled artisan will appreciate that the material, size, arrangement, and number of tubes can vary with the application for the bioreactor, but preferably have an inside diameter of at least 2 millimeters and wall thickness of at least 100 microns.

The hollow tube inlet port 20 is in communication with the intratubular space 40, via hollow tube perfusion inlet compartment 32, and is configured to admit a fluid into the intratubular space. The hollow tube outlet port 22 is in communication with the intratubular space, via hollow tube perfusion outlet compartment 34, and is configured to exit the fluid. A skilled artisan will appreciate that the fluid can vary with the application for the bioreactor. For example, for freezing and thawing the bioreactor, the fluid can be an ultra-coolant substance, for example, helium or liquid nitrogen vapors; a warm solution, such as, physiological saline (0.9 percent potassium chloride); or a heated vapor, such as, steam. Furthermore, for oxygenating or providing heat to the biologically active material, the fluid can be an oxygen-enriched gas mixture, a warm oxygen-enriched perfluorocarbon solution, or a solution containing fluorocarbons saturated with a concentration of oxygen and carbon dioxide.

The hollow tube perfusion inlet compartment 32 is in communication with the intratubular space 40 and the hollow tube inlet port 20, and is configured to isolate the entering fluid from the internal chamber 14 and the intracapillary space 42. The hollow tube perfusion outlet compartment 34 is in communication with the intratubular space and the hollow tube outlet port 22, and is configured to isolate the exiting fluid from the internal chamber and the intracapillary space.

The bundle of hollow tubes 16 are arranged in the internal chamber to facilitate freezing or vitrification of the mixture by the ultra-coolant substance. Furthermore, they are arranged to enable rapid thawing of the previously frozen or vitrified bioreactor when flushed with a warm solution or vapor, and, if the hollow tubes are also gas-permeable, to provide integrated oxygenation of the biologically active material when flushed with oxygen or oxygen-enriched perfluorcarbon solution. Also, the solution can be warmed, thus providing integrated heating during culture or use as a bioartificial organ.

The arrangement of the ports, compartments, tubes, and fibers shown in FIGS. 1 and 2 are exemplary and a skilled artisan will appreciate that other arrangements are possible to achieve the functionality of the bioreactor described herein.

The method of using the bioreactor will now be described.

First, the mixture of a biologically active material suspended in a culture medium, and preferably together with a cryoprotectant solution, is admitted a into the internal chamber 14 via the cell inlet port 28.

The ultra-coolant substance is admitted through the hollow tube inlet port 20, into the hollow tube perfusion inlet compartment 32, through the intratubular space 40, into the hollow tube perfusion outlet compartment 34, and out of the hollow tube outlet port 22. The number, size, diameter, and arrangement of the hollow tubes must be great enough to accommodate a sufficient volume of the cooling fluid in order to achieve a rapid cooling rate to avoid ice crystal formation to enable the cells or tissue to proceed directly to the glass stage. Because the hollow tubes 16 are in close contact with the biologically active material located within the internal chamber, the material will freeze or vitrify almost instantaneously, thereby maintaining viability of the biologically active material and avoiding ice crystal formation.

After the temperature of the biologically material is sufficiently frozen or vitrified, for example, down to −100° Celsius (C.), the bioreactor can then be placed into a cooler for storage, by submerging it into a cryogenic bath at a temperature of, for example, −130° C.

Alternately, if the unit is being prepared for long-term storage purposes, then the hollow tube inlet port 20 and the hollow tube outlet port 22 can be opened and the unit submerged into liquid nitrogen, which facilitates the flow of the liquid nitrogen into the hollow tube inlet port and the hollow tube outlet port, thereby filling the hollow tubes 16. The bioreactor can remain in the liquid nitrogen until it is ready to use.

To rapidly thaw the vitrified bioreactor, the hollow tubes 16 can be flushed with a warm solution or vapor, such as, 37° C. saline.

During culture or use as a bioartificial organ, the hollow fibers 18 can be perfused with either culture medium, plasma, or blood. Optionally, the hollow tubes 16 can be perfused continuously with either an oxygen-enriched gas mixture or with warm oxygen-enriched enriched perfluorocarbon solution to provide oxygen to the biologically active component, provided the tubes are gas-permeable, and to maintain the temperature at, for example, 37° C.

In the illustrated embodiment, the housing and tubes are substantially cylindrical in shape and elongated, and, the ports are disposed at or near the ends of the housing. Those skilled in the art will recognize that various modifications and variations can be made in the bioreactor of the present invention and in construction and operation of this bioreactor without departing from the scope or spirit from this invention. For example, one of ordinary skill in the art will appreciate that other shapes and materials could be used to obtain the features and performance of the invention as described above.

In conclusion, the bioreactor described herein provides a prefabricated and seeded bioreactor which is ready-to-use once thawed.

What is claimed is:

1. A bioreactor comprising:
    a shell defining an internal chamber;
    a cell inlet port, in communication with the internal chamber, configured to admit a mixture of biologically active material suspended in a culture medium into the internal chamber;
    a cell outlet port, in communication with the internal chamber, configured to exit the mixture from the internal chamber;
    a bundle of liquid-permeable hollow fibers defining an intracapillary space, disposed within the internal chamber;
    a hollow fiber inlet port, in communication with the intracapillary space, configured to admit a perfusate into the intracapillary space;
    a hollow fiber outlet port, in communication with the intracapillary space, configured to exit the perfusate from the intracapillary space;
    a bundle of liquid-impermeable hollow tubes defining an intratubular space, disposed within the internal chamber;
    a hollow tube inlet port, in communication with the intratubular space, configured to admit an ultra-coolant substance into the intratubular space;
    a hollow tube outlet port, in communication with the intratubular space, configured to exit the ultra-coolant substance;
    wherein the bundle of liquid-impermeable hollow tubes are arranged in the internal chamber to facilitate freezing or vitrification of the mixture by the ultra-coolant substance flowing through the intratubular space.

2. The bioreactor of claim 1 further comprising a hollow tube perfusion inlet compartment, in communication with the intratubular space and the hollow tube inlet port, configured to isolate the entering ultra-coolant substance from the internal chamber and the intracapillary space.

3. The bioreactor of claim 2, further comprising a hollow tube perfusion outlet compartment, in communication with the intratubular space and the hollow tube outlet port, configured to isolate the exiting ultra-coolant substance from the internal chamber and the intracapillary space.

4. The bioreactor of claim 1 further comprising a hollow fiber perfusion inlet compartment, in communication with the intracapillary space and the hollow fiber inlet port, configured to isolate the entering perfusate from the internal chamber and the intratubular space.

5. The bioreactor of claim 4 further comprising a hollow fiber perfusion outlet compartment, in communication with the intracapillary space and the hollow fiber outlet port, configured to isolate the exiting perfusate from the internal chamber and the intratubular space.

6. The bioreactor of claim 1, wherein the ratio of the quantity of the liquid-impermeable hollow tubes is less than the quantity of the liquid-permeable hollow fibers.

7. The bioreactor of claim 6, wherein the ratio of the quantity of the liquid-impermeable hollow tubes and the quantity of the liquid-permeable hollow fibers is about 1:0.

8. The bioreactor of claim 1, wherein the inside diameter of the liquid-impermeable hollow tubes is greater than the inside diameter of the liquid-permeable hollow fibers.

9. The bioreactor of claim 8, wherein the liquid-impermeable hollow tubes have an internal diameter of at least 2 millimeters and wall thickness of at least 100 microns.

10. The bioreactor of claim 9, wherein the liquid-impermeable hollow tubes are composed of silicone.

11. The bioreactor of claim 9, wherein the liquid-permeable hollow fibers have an inside diameter of at least 500 microns and a wall thickness of at least 50 microns.

12. The bioreactor of claim 1, wherein the liquid-permeable hollow fibers are composed of poly-sulifone.

13. The bioreactor of claim 1, wherein the cell inlet port is further configured to admit the mixture also including a cryoprotectant solution.

14. The bioreactor of claim 13, wherein the cryoprotectant solution is methylsulfoxide.

15. The bioreactor of claim 1, wherein the hollow tubes are also gas-permeable.

16. The bioreactor of claim 15, wherein the liquid-impermeable, gas-permeable hollow tubes are composed of Teflon.

17. The bioreactor of claim 1, wherein the hollow tubes are also gas-impermeable.

18. The bioreactor of claim 17, wherein the liquid-impermeable, gas-permeable hollow tubes are composed of silicone.

19. A method of making a ready-to-use bioreactor, the method comprising:
    providing a shell defining an internal chamber;
    arranging a bundle of liquid-impermeable hollow tubes within the internal chamber, the bundle of liquid-impermeable hollow tubes defining an intratubular space;
    providing a hollow tube inlet port in communication with the intratubular space;
    providing a hollow tube outlet port in communication with the intratubular space;
    providing a cell inlet port in communication with the internal chamber;
    admitting a mixture of a biologically active material suspended in a culture medium into the internal chamber via the cell inlet port; and
    perfusing an ultra-coolant substance into the intratubular space via the hollow tube inlet port and out of the intratubular space via the hollow tube outlet port sufficient to freeze or vitrify the mixture.

20. The method of claim 19, wherein the hollow tubes are also gas-impermeable.

21. The method of claim 19, wherein the mixture also includes a cryoprotectant solution.

22. The method of claim 19 further comprising:

arranging a bundle of liquid-permeable hollow fibers within the internal chamber, the bundle of liquid-permeable hollow fibers defining an intracapillary space and composed of a material capable of withstanding vitrification;

providing a hollow fiber inlet port in communication with the intracapillary space; and providing a hollow fiber outlet port in communication with the intracapillary space.

23. The method of claim 22 further comprising:

providing a hollow tube perfusion inlet compartment, in communication with the intratubular space and the hollow tube inlet port, configured to isolate intratubular space from the internal chamber and the intracapillary space;

providing a hollow tube perfusion outlet compartment, in communication with the intratubular space and the hollow tube outlet port, configured to isolate the intratubular space from the internal chamber and the intracapillary space;

providing a hollow fiber perfusion inlet compartment, in communication with the intracapillary space and the hollow fiber inlet port, configured to isolate the intracapillary space from the internal chamber and the intratubular space; and providing a hollow fiber perfusion outlet compartment, in communication with the intracapillary space and hollow fiber outlet port, configured to isolate the intracapillary space from the internal chamber and the intratubular space.

24. The method of claim 19 further comprising:

providing a cryogenic bath; and submersing the bioreactor in the cryogenic bath.

* * * * *

UNITED STATES PATENT AND TRADEMARK OFFICE
CERTIFICATE OF CORRECTION

PATENT NO.    : 6,242,248 B1
DATED         : June 5, 2001
INVENTOR(S)   : Rozga et al.

It is certified that error appears in the above-identified patent and that said Letters Patent is hereby corrected as shown below:

Column 4,
Line 27, please delete "perfluorcarbon" and insert therefor -- perfluorocarbon --.

Column 6,
Line 17, please delete "1.0" and insert therefor -- 1:10 --.
Line 31, please delete "poly-sulifone" and insert therefor -- polysulfone --.
Line 45, please delete "gas-permeable" and insert therefor -- gas-impermeable --.

Column 7,
Line 19, please delete "isolate intratubular space" and insert therefor -- isolate the intratubular space --.

Signed and Sealed this

Third Day of June, 2003

JAMES E. ROGAN
*Director of the United States Patent and Trademark Office*